(12) United States Patent
Carson et al.

(10) Patent No.: US 11,806,112 B2
(45) Date of Patent: Nov. 7, 2023

(54) METHOD, SYSTEM, SOFTWARE, AND DEVICE FOR REMOTE, MINIATURIZED, AND THREE-DIMENSIONAL IMAGING AND ANALYSIS OF HUMAN LESIONS RESEARCH AND CLINICAL APPLICATIONS THEREOF

(71) Applicant: Pensievision, Inc., San Diego, CA (US)

(72) Inventors: Joseph Carson, Charleston, SC (US);
Sadik Esener, San Diego, CA (US);
Kimberly Liu, San Diego, CA (US);
David Melnick, Denver, CO (US);
Elyana Crowder, Atlanta, GA (US)

(73) Assignee: Pensievision, Inc., San Diego, CA (US)

( * ) Notice: Subject to any disclaimer, the term of this patent is extended or adjusted under 35 U.S.C. 154(b) by 780 days.

(21) Appl. No.: 16/304,281

(22) PCT Filed: May 25, 2017

(86) PCT No.: PCT/IB2017/000824
§ 371 (c)(1),
(2) Date: Nov. 24, 2018

(87) PCT Pub. No.: WO2017/203369
PCT Pub. Date: Nov. 30, 2017

(65) Prior Publication Data
US 2019/0090753 A1 Mar. 28, 2019

Related U.S. Application Data

(60) Provisional application No. 62/341,150, filed on May 25, 2016.

(51) Int. Cl.
*A61B 5/00* (2006.01)
*A61B 90/00* (2016.01)

(52) U.S. Cl.
CPC .......... *A61B 5/0084* (2013.01); *A61B 5/0073* (2013.01); *A61B 5/4331* (2013.01); *A61B 5/6853* (2013.01); *A61B 90/36* (2016.02)

(58) Field of Classification Search
CPC ......... G06T 7/40; G06T 7/44–46; G06T 7/50; G06T 7/507; G06T 7/514; G06T 7/521;
(Continued)

(56) References Cited

U.S. PATENT DOCUMENTS 6,201,899 B1 * 3/2001 Bergen ............... G06K 9/00134
382/106
6,211,904 B1 * 4/2001 Adair ................. A61B 1/00082
257/E25.032

(Continued)

OTHER PUBLICATIONS

Calin, Mihaela Antonina, Sorin Viorel Parasca, Roxana Savastru, Marian Romeo Calin, and Simona Dontu. "Optical techniques for the noninvasive diagnosis of skin cancer." Journal of cancer research and clinical oncology 139, No. 7 (2013): 1083-1104.*

(Continued)

*Primary Examiner* — Carolyn A Pehlke
(74) *Attorney, Agent, or Firm* — Alexander R. Schlee; Pascal A. Schlee; Schlee IP International, PC

(57) ABSTRACT

A system, device, and accompanying software for the remote, three-dimensional, and high-throughput imaging and analysis of human lesions, across a range of wavelengths, lens radii and imaging sensors. This system, device, and software generates and analyses of tumor images at infrared wavelengths through the use of miniaturized, liquid lenses. It has a number of clinical, diagnostic, research, and other imaging applications, including the remote, three-dimensional, and high-throughput imaging and analysis of human cancer tumors.

16 Claims, 8 Drawing Sheets

(58) Field of Classification Search
CPC ........... G06T 7/529; G06T 7/536; G06T 7/55; G06T 7/557; G06T 7/564; G06T 7/571; G06T 7/579; G06T 7/586; G06T 7/593; G06T 7/596; A61B 1/00009; A61B 1/05; A61B 5/0064; A61B 5/0075; A61B 5/0084; A61B 90/36; A61B 5/0082; A61B 5/0059

See application file for complete search history.

(56) References Cited

U.S. PATENT DOCUMENTS

| | | | | |
|---|---|---|---|---|
| 9,196,070 | B2* | 11/2015 | Matsumoto | G06T 11/60 |
| 2005/0094859 | A1 | 5/2005 | Ruth et al. | |
| 2007/0135803 | A1* | 6/2007 | Belson | A61B 1/00128 606/1 |
| 2010/0289819 | A1 | 11/2010 | Singh et al. | |
| 2012/0113525 | A1* | 5/2012 | Kong | G02B 26/004 359/665 |
| 2013/0237841 | A1* | 9/2013 | Freeman | A61B 5/0064 600/473 |
| 2014/0009572 | A1* | 1/2014 | Matsumoto | H04N 5/23238 348/36 |
| 2014/0039277 | A1 | 2/2014 | Abraham | |
| 2015/0327753 | A1 | 11/2015 | Amirana et al. | |
| 2016/0338590 | A1* | 11/2016 | Sagalovich | A61B 5/0013 |
| 2017/0010456 | A1* | 1/2017 | Gopinath | G02B 6/06 |

OTHER PUBLICATIONS

Thekkek, Nadhi, and Rebecca Richards-Kortum. "Optical imaging for cervical cancer detection: solutions for a continuing global problem." Nature Reviews Cancer 8, No. 9 (2008): 725-731.*

Jayachandran, Maanasa, Suset Rodriguez, Elizabeth Solis, Jiali Lei, and Anuradha Godavarty. "Critical review of noninvasive optical technologies for wound imaging." Advances in wound care 5, No. 8 (2016): 349-359.*

Wang, Yu-Jen, et al. "Extended depth-of-field 3D endoscopy with synthetic aperture integral imaging using an electrically tunable focal-length liquid-crystal lens." Optics letters 40.15 (2015): 3564-3567.*

Hassanfiroozi, Amir, et al. "Dual layer electrode liquid crystal lens for 2D/3D tunable endoscopy imaging system." Optics express 24.8 (2016): 8527-8538.*

Iizuka, Keigo. "Omnifocus laparoscope." Applied Optics 52.33 (2013): 7904-7911.*

Kagawa, Keiichiro, et al. "Variable field-of-view visible and near-infrared polarization compound-eye endoscope." 2012 Annual International Conference of the IEEE Engineering in Medicine and Biology Society. IEEE, 2012.*

D.V. O'Donnell, "An Infrared Survey of Galaxy Clusters with the Spitzer Space Telescope", McGill University, 2008, p. 62.

Schuster, M. T., Marengo, M., & Pattern, B. M. . (2006). "IRACproc: a software suite for processing and analyzing Spitzer/IRAC data". 6270, p. 20. SPIE. <https://lweb.cfa.harvard.edu/irac/publications/2006other/Schuster.pdf>.

* cited by examiner

METHOD, SYSTEM, SOFTWARE, AND DEVICE FOR REMOTE, MINIATURIZED, AND THREE-DIMENSIONAL IMAGING AND ANALYSIS OF HUMAN LESIONS RESEARCH AND CLINICAL APPLICATIONS THEREOF

CROSS-REFERENCE TO RELATED APPLICATIONS

This application claims the benefit of U.S. Provisional No. 62/341,150, filed on May 25, 2016, which is incorporated herein by reference.

BACKGROUND OF THE INVENTION

There is an unmet need for cancer imaging technologies in resource-scarce areas, and there is an unmet need for the early detection of cancer tumors in humans. The prior art describes existing methods for tumor imaging in humans.

The early detection of primary and recurrent diseases is critical for the survival of patients with malignant tumors. A failure of early detection invariably leads to patient death. For many invasive cancers, including lung cancer, colon cancer, and ovarian cancer, no technology exists in the prior art capable of providing consistent early detection of malignant tumors.

Endoscopy is a useful tool for tumor evaluation, but not for routine screening, as it is relatively invasive and its operation requires special training. In addition, the experience of an endoscopist is critical for cancer detection, particularly when the disease is at the early stage.

The oncology application of modern endoscopy includes detection, characterization, and removal of neoplastic lesions. Despite substantial technical improvements during these years, inadequate visualization, misinterpretation, and lesion subtlety all lead to the continued suboptimal detection and evaluation of early malignancies. While numerous new techniques have emerged, each only focuses on one aspect of the shortcomings, which could exacerbate another aspect of problems. Generally, broad-field technologies have higher sensitivity for lesion detection, whereas small-field technologies have higher specificity to identify abnormal lesions. Therefore, the choice of which technologies would be related to the matter of interest for detection, characterization or confirmation. Some of these techniques have been widely available in clinical settings, such as dye-based or digital chromoendoscopy. On the other hand, confocal laser endomicroscopy and endocytoscopy, optical coherence tomography (OCT), autofluorescence, and spectroscopy-based imaging are generally applicable only in a research setting. In general, there is an inverse relationship between tissue penetration and image resolution for these techniques. Besides, the tradeoff between a lens magnification and the field of view is another practical issue associated with techniques for subcellular imaging; therefore a target lesion has to be first identified using other broad-field techniques.

Furthermore, current standard endoscopes provide two dimensional images, which are not desirable for endoscope-based intervention, especially in delicate spaces. For this reason, many neurosurgeons prefer, for transcranial skull base operations, using a microscope that enables three dimensional visualization, rather than an endoscope. To restore 3D perception, a company (Visionsense) introduced a camera that "imitates the eye of a bee" at the tip of an endoscope. However, this system only provides limited stereoscopic images for improving 3D perception for the endoscope operator, and leaves out important detailed depth information for many other applications.

All current endoscopic techniques are heavily dependent on the skill and experience of the operators. Even with video recording, a lesion will be missed when the endoscopist does not recognize it, because the missed lesion would not be in focus. Recently, we have been developing a 3D imaging system[6] to mitigate this fundamental problem by applying refocus technologies (e.g. light field photography). Importantly, this imaging platform can potentially incorporate most of the new endoscopic techniques previously described.

A conventional camera captures an object from a single point in space. Therefore, it records the directionally varying illumination on the object, but does not capture the spatially varying illumination from one location to another. Alternatively, a light field camera captures the spatially varying appearance of an object and the surroundings by recording a 2D array of images across a surface, which can be computationally constructed to become a 3D structure by tracing light rays to the original capture surface. To obtain such a 2D array of images, various designs have been reported, including the use of camera gantries, camera arrays, lenslet arrays, and coded aperture methods. Technically, this 2D array of images can also be captured by moving a single camera over each position of a 2D matrix plane. While a single-camera, multi-shot approach is usually cheaper to set up for capturing light-field properties of static objects, a multi-camera setup or single-image multiplexing (e.g. using a single-camera with a micro-lens array) is required to capture more dynamic events.

Traditionally, a three dimensional image can be reconstructed from multiple 2D images by using a focus stacking technique, or by applying a laser range sensor or Kinect sensor. While these approaches may create 3D "perception", it generally cannot provide detailed depth information for an object and the surrounding environment. Compared to these methods, light field imaging can conveniently offer a densely sampled depth map for the construction of a detailed 3D model.

The prior art also includes infrastructure-intensive technologies for the early detection of tumors that are not overly invasive. This includes technology for the early detection of skin cancer, breast cancer, and prostate cancer. Magnetic resonance imaging ("MRI") and computerized axial tomography scanning ("CAT-Scan") technology are the most prominent among the early cancer detection tools in the prior art. These technologies can be used to generate three-dimensional images of human cancer tumors.

The prior art available for the early detection of malignant tumors, including CAT and MRI technology, require the application of substantial resources and highly-trained personnel. Most medical institutions cannot afford this infrastructure-intensive technology. Uninsured patients, lower-income patients, and patients located in resource-scarce areas cannot easily access this prior art, resulting in the failure to detect the malignant tumors before metathesis and eventual patient death.

Imaging technologies in the prior art that have not yet been applied to the field of medicine may be applicable to the early detection of malignant tumors. For instance, the light-field camera developed by Lytro, Inc. may be useful in generating and analyzing three-dimensional images of external tumors, such as tumors on the skin or in the mouth.

The prior art includes limited applications of infrared imaging technology to the screening of malignant tumors.

For instance, digital infrared thermal imaging is a thermography application used to image breast cancer.

The prior art includes miniaturized cameras for imaging of diseases within the human body. For instance, miniaturized flow cytometry-based immunoassays have been applied for the detection of leptomeningeal disease.

While the prior art consists, in part, of various three-dimensional imaging, infrared, and miniaturized technologies for the detection and analysis of malignant tumors in humans, it does not consist of any technology combining three-dimensional, infrared, and miniaturized innovations for detecting, imaging, or analyzing malignant tumors in humans.

The prior art consists of software used to segment, highlight, and analyze cross-sections of tumors imaged using technology also available in the prior art. This software is capable of rendering three-dimensional images of tumors for high-level analysis.

The prior art also consists of noise-reducing analysis software applied to astronomical imaging. This software renders clearer images of pictures taken in outer space by reducing the amount of background noise created by the Earth's' sky and atmosphere. The image-rendering capabilities of this software have been refined and improved over time to generate clearer images of astronomical bodies. However, this astronomical image-rendering software has not yet been applied to the imaging and analysis of tumors.

SUMMARY OF THE INVENTION AND DESCRIPTION OF THE DRAWINGS

The disclosure comprises a device and accompanying software for the three-dimensional imaging and analysis of human lesions. The device consists of an imaging lens that facilitates the transmission of emitted light across a range of wavelengths, a means of communicating the resulting images remotely, and accompanying software to resolve and analyze those images. In its preferred embodiment, the present disclosure's device is miniaturized, facilitates the transmission of emitted infrared light, and transmits the resulting images for remote analysis by the accompanying software. The disclosure may be applied to a number of clinical, research, and other oncological uses, including to generate and resolve images of early-stage, internal human cancers.

In some instances, the disclosure is used for the imaging of invasive tumors such as those in the inner ear or accessible via the artery. For these uses, a fiber bundle dynamic focusing lens assembly integrates a dual-layer-encased fiber bundle coupled with a fluidic focusing lens ("FFL") and a conventional digital camera for generating endoscopic, all-focus, three-dimensional tumor images. Here, the diameter of the endoscope unit ranges from two to fifteen millimeters, and the camera component is attached externally. The FFL, which is capable of variable focusing in different instances, consists of a bendable membrane suspended by two washers over the front of the fiber bundle. The focal length of the FFL is controlled by fluid pressure on the lens membrane. As displayed in attached FIG. 2, the pressurized fluid is delivered via the spacing between the fiber bundle protecting sheet and the endoscope cover layer. As the fluid pressure is adjusted, multiple focal lengths are achieved, and the camera captures a snapshot at each setting. The resulting tumor image transmits through the FFL onto the fiber bundle front surface, and finally into the external camera where a variety of imaging and spectral techniques may be enabled. such as standard optical imaging, dual-narrowband imaging, spectroscopy, or multi-wavelength imaging from infrared through ultraviolet. Additional optical functionalities, such as wide-field or zoomed-in imaging, may be achieved by attaching optics to the front of the FFL.

In some instances, the FFL assembly may be coupled with various types of software for rendering and analysis of collected images and for the remote transmission of those images to users worldwide. FIGS. 1-2, attached, diagram an embodiment of the present disclosure that uses a miniaturized camera that uses infrared light to capture infrared three-dimensional images of early-stage tumors. The camera can be operated remotely and transmit the resulting images anywhere in the world.

FIG. 3 diagrams a surface view of the fiber bundle dynamic focusing lens. The figure designates the lens membrane and the fiber-optic bundles for image capture and illumination.

FIG. 4 diagrams a longitudinal cross-section top view of the fiber bundle dynamic focusing lens. The figure designates the lens membrane, the liquid outside the fiber bundle unit that connects to the space below the membrane, and the fiber-optic bundles for image capture and illumination.

FIG. 5 diagrams a longitudinal cross-section bottom view of the fiber bundle dynamic focusing lens. This figure also designates the lens membrane, the liquid outside the fiber bundle unit that connects to the space below the membrane, and the fiber-optic bundles for image capture and illumination.

In some instances, the disclosure is used to image and analyze external human tumors, including tumors of the skin and cervix. FIG. 6 diagrams this embodiment, using the same fiber optic bundle lens assembly described in FIGS. 1-5, only insider a larger enclosure. The enclosure is an inflatable, plastic balloon which can be increased or decreased in size through the application of air pressure.

In some instances, software that is part of the disclosure and coupled to the disclosure's device renders and analyzes the images collected. The software carries out the task by implementing a version of a Maximum-Local-Derivative (MLD) algorithm that has previously been successfully used to extract sharpness information for large-scale data sets collected with NASA's Spitzer Space Telescope. The code begins by reading in a set of images, where each frame was collected with a unique focus setting and within a fraction of a second from each other. Evaluating the sharpness of focus, it remaps individual image parts onto a single array, thus combining the image set to produce a single, sharp, all-focus image.

FIG. 6 also diagrams a conceptual design of the embodied enclosure described in Paragraph 0035, above, for imaging of lesions in the human cervix. The cross sections displayed in FIG. 6 include an inflatable balloon, manual control air pumps, an external camera module, and tubes connecting the various components to one another.

FIG. 7 diagrams an embodiment based on the model diagramed in FIG. 6, consisting of an 18×18×6 mm tunable liquid lens aligned with an endoscope 10 mm in diameter using a 3D printed enclosure. The liquid lens is similar to the embodiments described in FIGS. 1-5, is electrically tunable, and includes two transparent liquids, such as water and oil, that are placed between two electrodes. An electric field is applied on the electrodes to change the shape of the hydrophobic liquid droplet included within, which in turn changes the focusing point of the lens. In this embodiment, the lens is controlled by a software driver that directs the focus setting for the collection of images multiple tumor images. The accompanying software processes the images for three-dimensional viewing and rendering in real time. The present disclosure may include embodiments similar to the one diagramed in FIG. 1, but on a smaller or miniaturized scale.

FIG. 8 diagrams an x-ray view of the embodiment described in FIG. 1.

FIG. 9 displays the application of the embodiment described in FIG. 1 as applied to the imaging of human cervical cancer. The embodiment is shown being tested on a gynecological manikin.

The above description of the disclosed embodiments is provided to enable any person skilled in the art to make or use the present disclosure. Various modifications to these embodiments will be readily apparent to those skilled in the art, and the generic principles described herein can be applied to other embodiments without departing from the spirit or scope of the present disclosure. Thus, it is to be understood that the description and drawings presented herein represent a presently preferred embodiment of the present disclosure and are therefore representative of the subject matter, which is broadly contemplated by the present disclosure. It is further understood that the scope of the present disclosure fully encompasses other embodiments that may become obvious to those skilled in the art.

BRIEF DESCRIPTION OF THE DRAWINGS

The embodiments are illustrated by way of example and not limitation in the figures of the accompanying drawings in which like references indicate like elements.

FIG. 9 illustrates a diagram of components used by the present disclosure, in accordance with an embodiment of the present disclosure.

Figure 1:
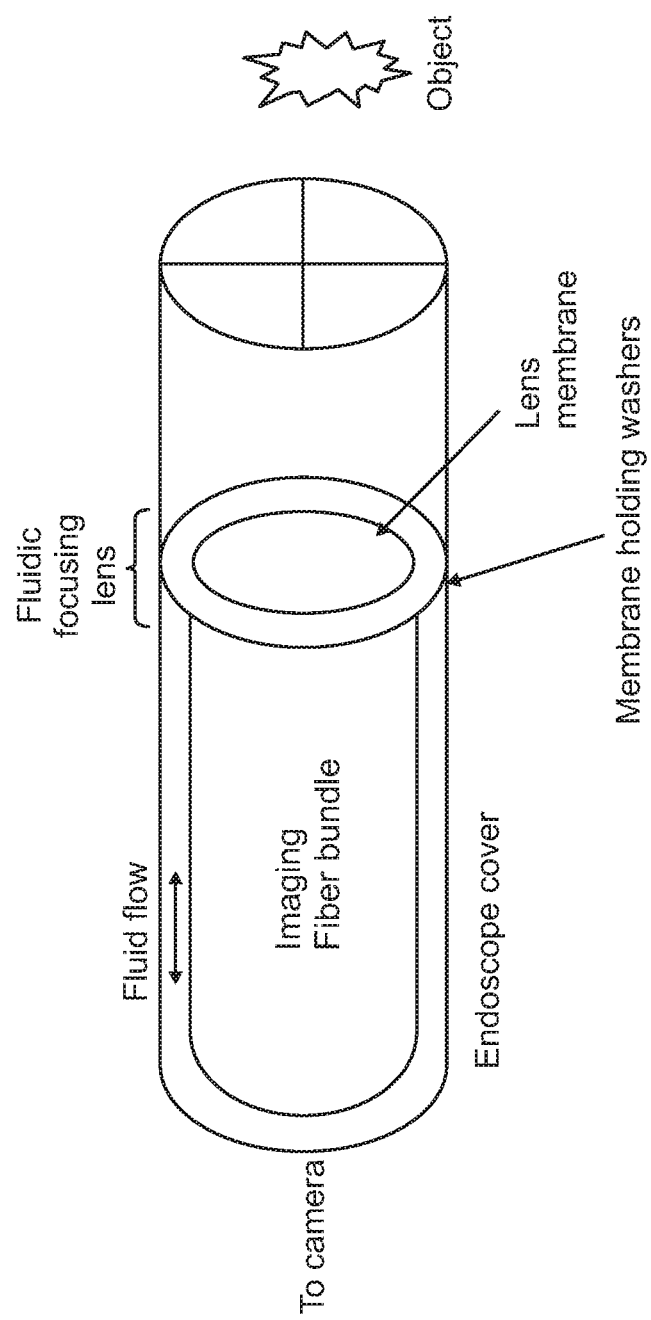
FIG. 1 illustrates a diagram of a process used by the present disclosure, in accordance with an embodiment of the present disclosure.
Figure 2:
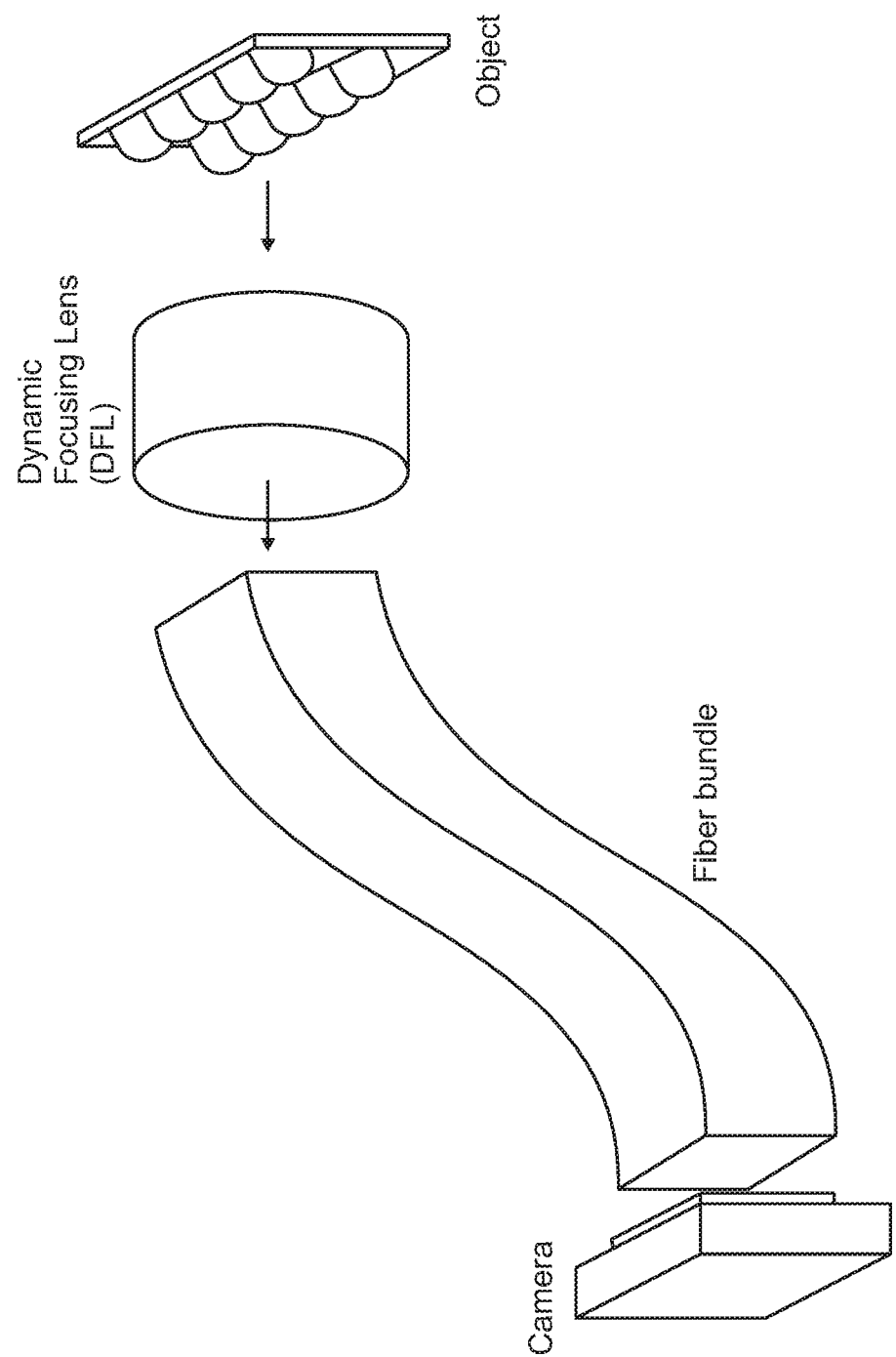
FIG. 2 illustrates another diagram of a process used by the present disclosure, in accordance with an embodiment of the present disclosure.
Figure 3:
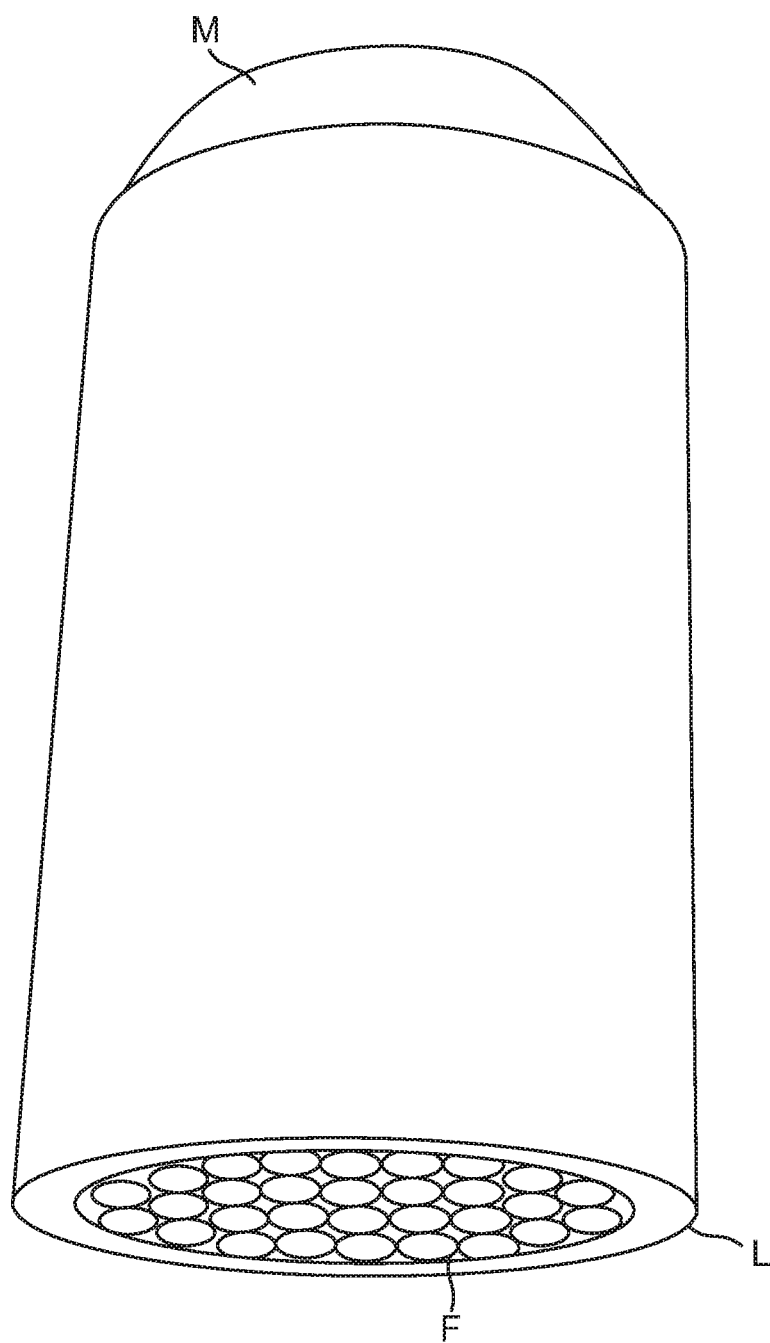
FIG. 3 illustrates a diagram of a structure used by the present disclosure, in accordance with an embodiment of the present disclosure.
Figure 4:
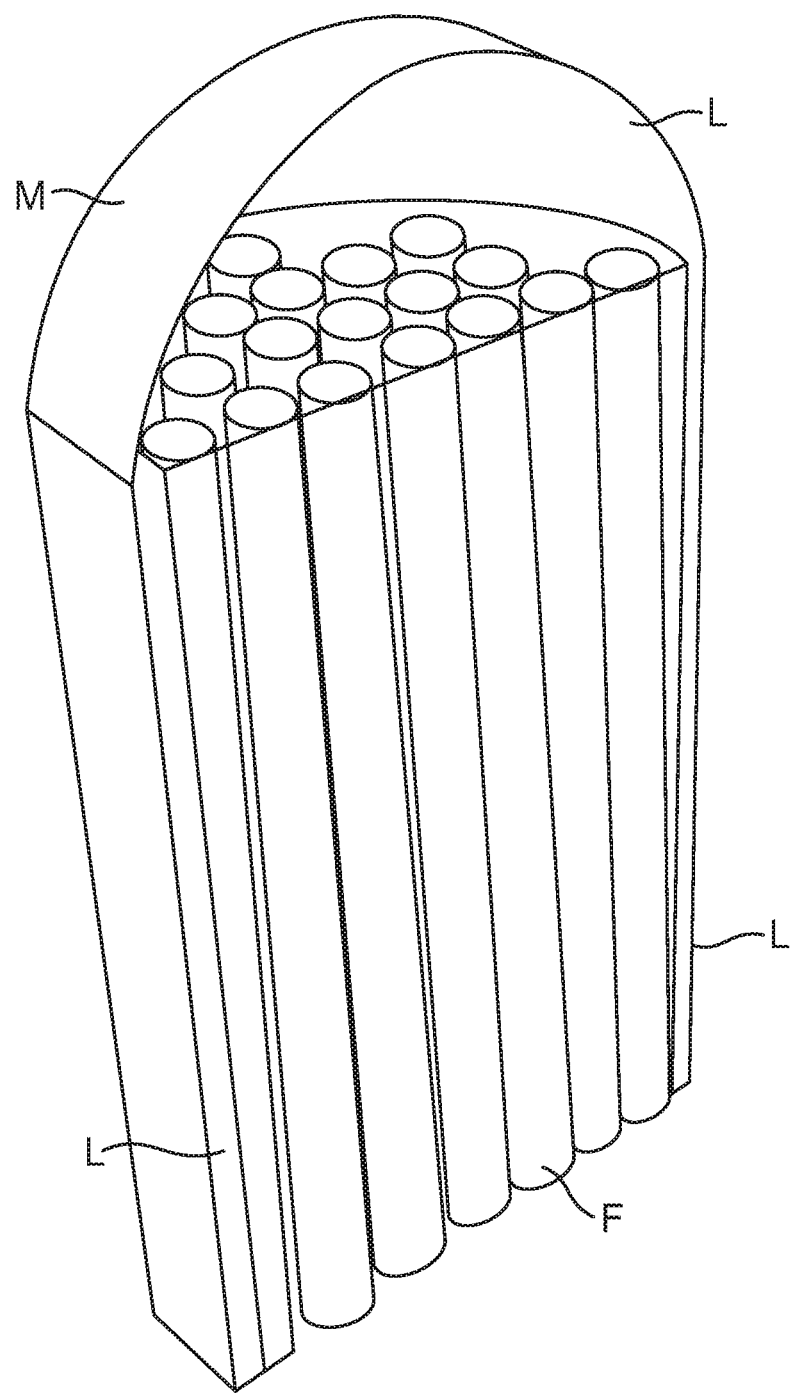
FIG. 4 illustrates a diagram of another structure used by the present disclosure, in accordance with an embodiment of the present disclosure.
Figure 5:
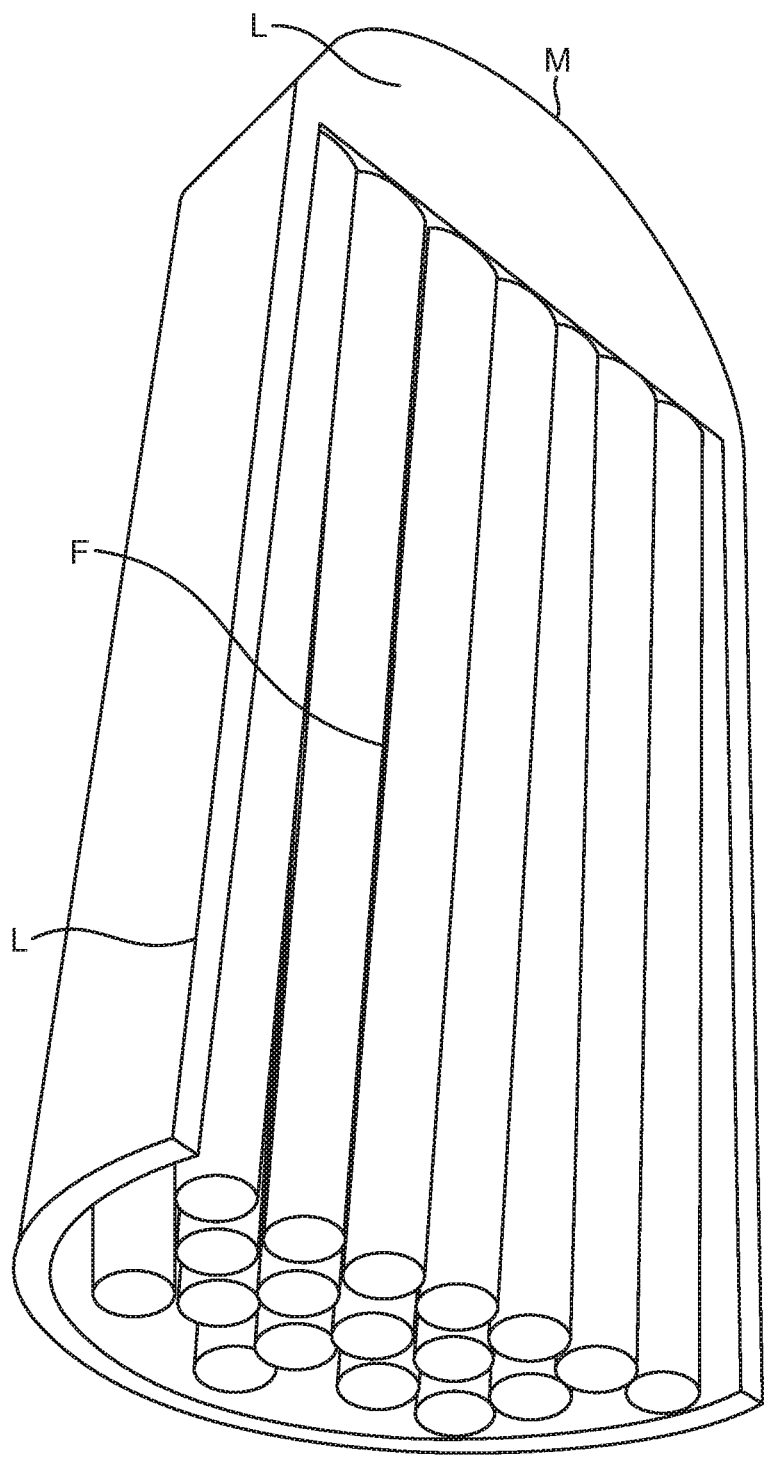
FIG. 5 illustrates a diagram of another structure used by the present disclosure, in accordance with an embodiment of the present disclosure.
Figure 6A:
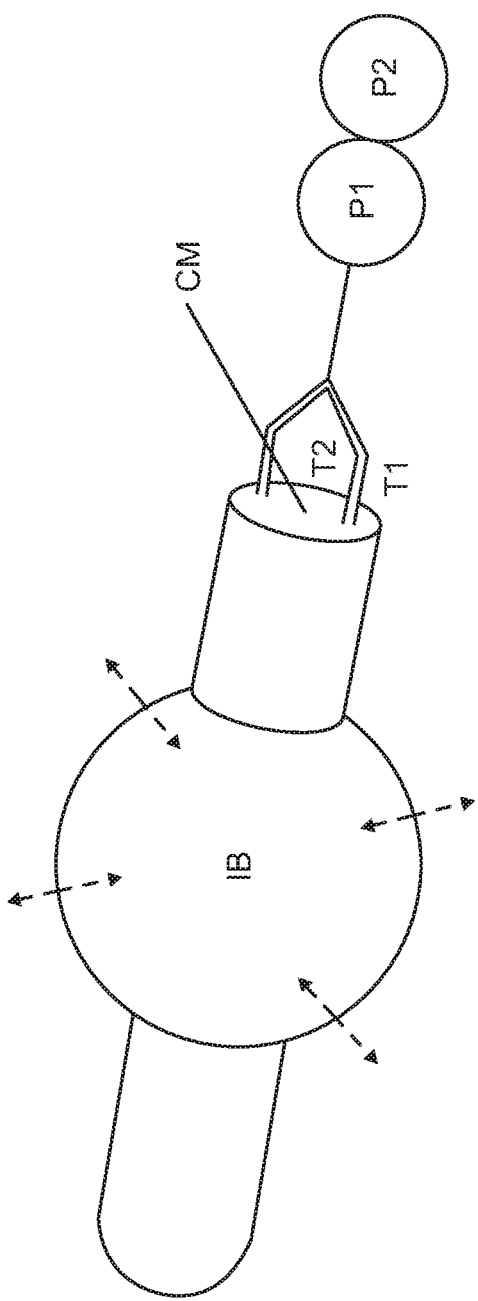
FIG. 6 illustrates a diagram of another structure used by the present disclosure, in accordance with an embodiment of the present disclosure.
Figure 6B:
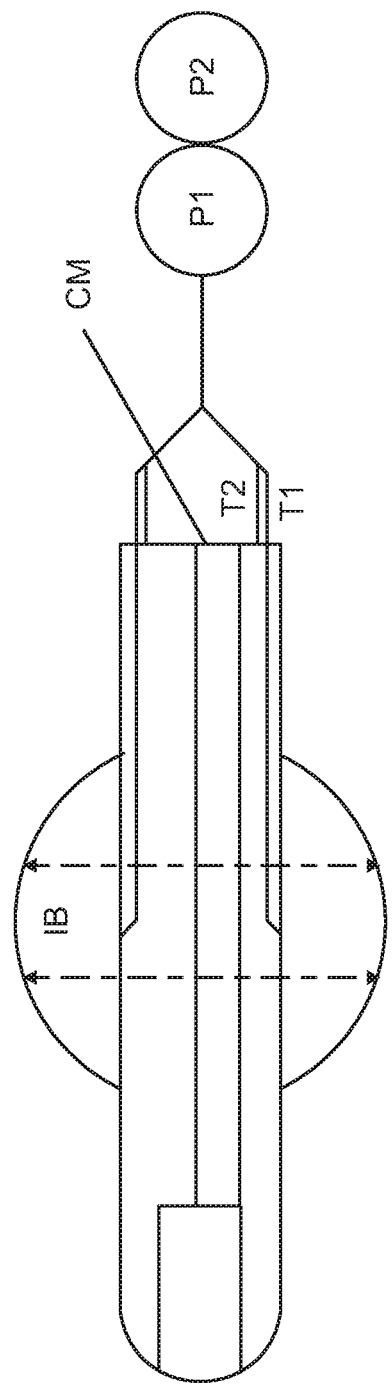
Figure 7:
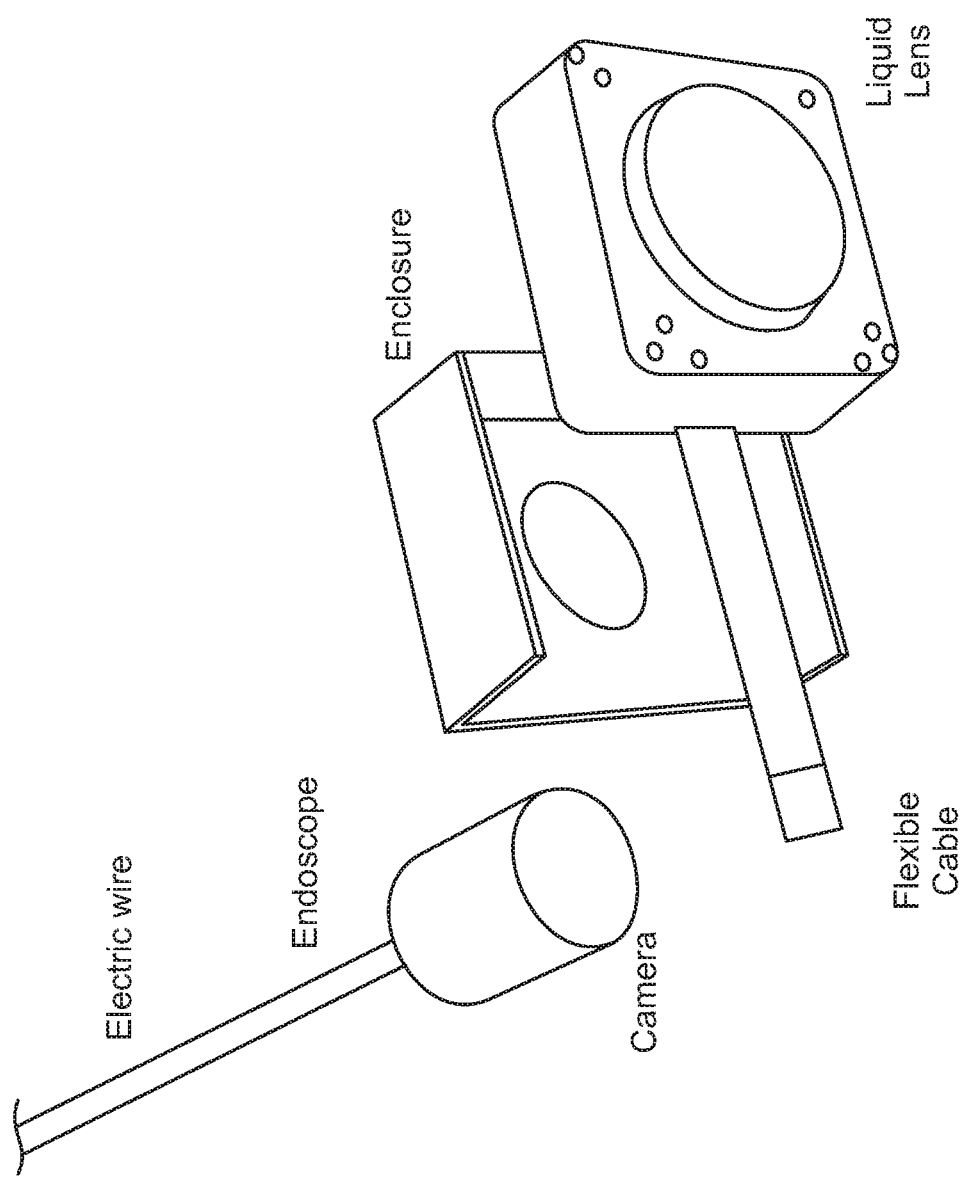
FIG. 7 illustrates a diagram showing a relationship in accordance with an embodiment of the present disclosure.
Figure 8:
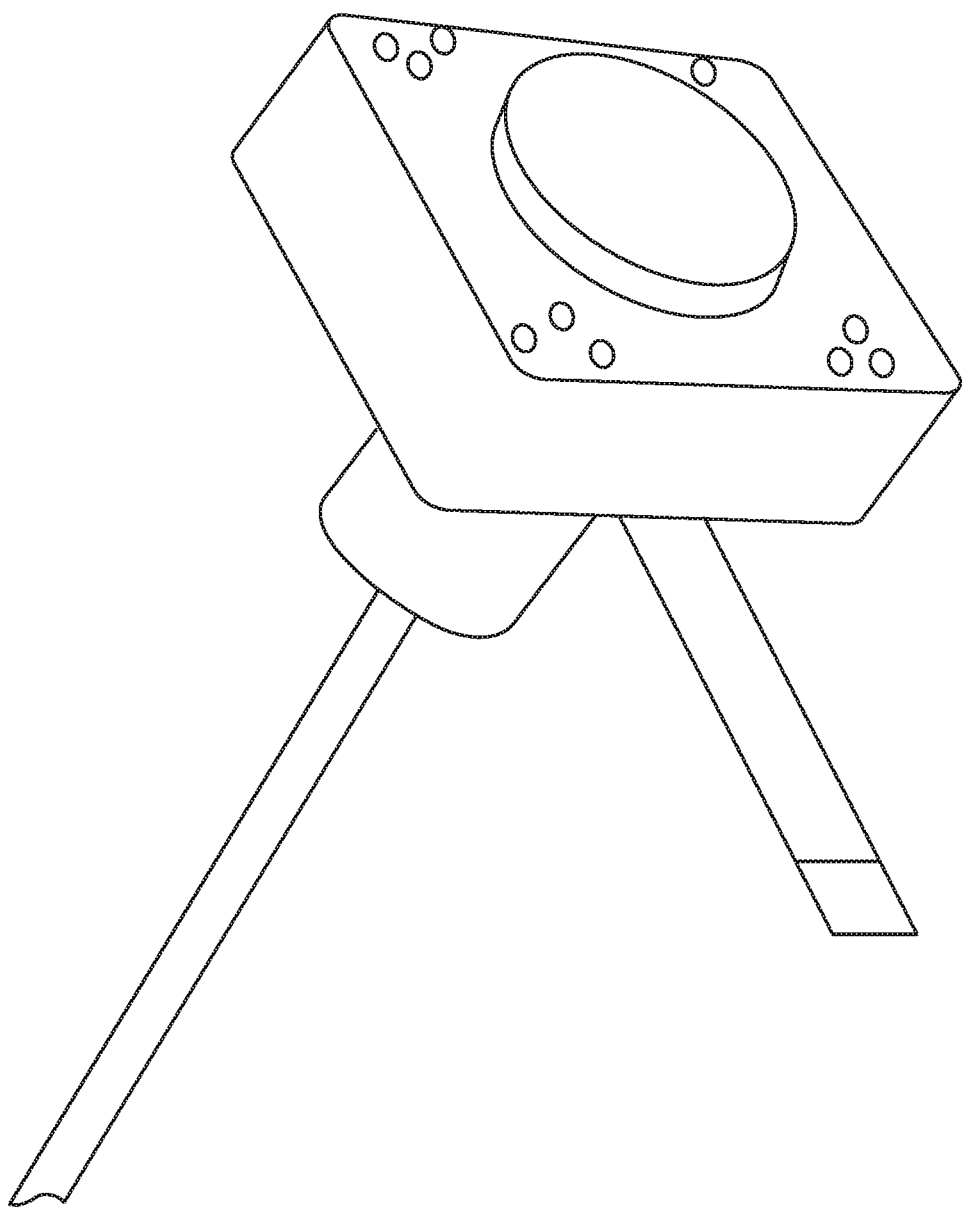
FIG. 8 illustrates a diagram showing another relationship in accordance with an embodiment of the present disclosure.

What is claimed is:

1. A system for the imaging and analysis of human lesions, comprising:
   an illumination component emitting illumination light;
   fiber-optic bundles for image capture and illumination, said fiber-optic bundles having a proximal end and a distal end and facilitates the transmission of the emitted illumination light in a direction from the proximal end to the distal end;
   an imaging camera at the proximal end of the fiber optic bundles;
   an electrically tunable liquid imaging lens connected to the distal end of the fiber-optic bundles in a light transmitting fashion transmitting light to the camera, the electrically tunable liquid imaging lens comprising a transparent, flexible substrate encompassing at least two liquids;
   an enclosure, said enclosure housing the electrically tunable liquid imaging lens, illumination component, and the imaging camera; and
   a driver accompanying the electrically tunable liquid imaging lens, wherein the driver is configured to control the effective focus of the electrically tunable liquid imaging lens, enabling the imaging camera to capture lesion images within a fraction of a second from each other across a range of focus settings in order to produce a single, sharp, all-focus image.

2. The system according to claim 1, where the wavelength emitted by the illumination component is infrared.

3. The system according to claim 1, where the wavelength emitted by the illumination component is ultraviolet.

4. The system according to claim 1, where the wavelength emitted by the illumination component is visible.

5. The system according to claim 1, where the electrically tunable liquid imaging lens used is twenty millimeters in diameter.

6. The system according to claim 1, where the electrically tunable liquid imaging lens used is two to fifteen millimeters in diameter.

7. The system according to claim 1, where the electrically tunable liquid imaging lens used is less than two millimeters in diameter.

8. The system according to claim 1, where the enclosure is a plastic balloon that can be inflated or deflated, and increased or decreased in size, through the application of air pressure.

9. The system according to claim 8, wherein the enclosure is configured to protect all optical and electronic components of the system for the imaging and analysis of human lesions from the outside environment.

10. The system according to claim 1, where the system is configured to take all-focus, three dimensional snapshots of external lesions on the human body.

11. The system according to claim 10, where the system is configured to image external lesions including skin, cervical, mouth, throat, and anal cancers.

12. The system according to claim 10, where the system is configured to image and evaluate external lesions including infected wounds and traumatic injury wounds.

13. The system according to claim 1, wherein the fiber-optic bundles are bendable.

14. The system according to claim 1, wherein the system is used to image and analyze human lesions located in confined spaces.

15. The system according to claim 14, where the lesions are located in the ear canal or are accessed via the arterial canal.

16. The system according to claim 1, further comprising a fiber bundle protecting sheet encompassing the fiber bundles, an endoscope cover layer, and a spacing between the fiber bundle protecting sheet and the endoscope cover layer through which pressurized fluid is delivered to modulate the focus settings of the electrically tunable liquid imaging lens.

* * * * *